(12) United States Patent
Wyrick

(10) Patent No.: US 12,097,318 B2
(45) Date of Patent: Sep. 24, 2024

(54) POST OPERATION MASTECTOMY BRA

(71) Applicant: Three Strands Recovery Wear Corporation, Salisbury, NC (US)

(72) Inventor: Leah Brooke Wyrick, Salisbury, NC (US)

(73) Assignee: Three Strands Recovery Wear Corporation, Salisbury, NC (US)

(*) Notice: Subject to any disclaimer, the term of this patent is extended or adjusted under 35 U.S.C. 154(b) by 254 days.

(21) Appl. No.: 17/381,878

(22) Filed: Jul. 21, 2021

(65) Prior Publication Data

US 2021/0346591 A1 Nov. 11, 2021

Related U.S. Application Data

(63) Continuation of application No. PCT/US2020/014387, filed on Jan. 21, 2020.

(60) Provisional application No. 62/794,767, filed on Jan. 21, 2019.

(51) Int. Cl.
*A41C 3/00* (2006.01)
*A61F 5/03* (2006.01)
*A61M 1/00* (2006.01)

(52) U.S. Cl.
CPC .......... *A61M 1/985* (2021.05); *A41C 3/0028* (2013.01); *A61F 5/03* (2013.01); *A61M 1/60* (2021.05); *A61M 1/912* (2021.05); *A61M 2209/088* (2013.01); *A61M 2210/1007* (2013.01)

(58) Field of Classification Search
CPC ........ A41C 3/0064; A41C 3/0028; A61F 5/03

USPC .......................................................... 450/58
See application file for complete search history.

(56) References Cited

U.S. PATENT DOCUMENTS

| | | | |
|---|---|---|---|
| 2,389,410 A | 11/1945 | Butow | |
| 4,630,610 A | 12/1986 | Fletcher | |
| 5,257,956 A | 11/1993 | Ewen | |
| 6,477,710 B1 | 11/2002 | Ojoyeyi | |
| 9,161,574 B2 | 10/2015 | Swendseid et al. | |
| 2006/0019576 A1 | 1/2006 | Bell et al. | |
| 2006/0194509 A1 | 8/2006 | Patterson | |
| 2008/0294128 A1 | 11/2008 | Richards | |
| 2013/0254970 A1 | 10/2013 | Curran et al. | |
| 2014/0196189 A1* | 7/2014 | Lee | A61F 5/449 2/69 |

(Continued)

OTHER PUBLICATIONS

International Search Report and Written Opinion for Application No. PCT/US 20/14387 dated Mar. 10, 2020.

*Primary Examiner* — Timothy K Trieu

(74) *Attorney, Agent, or Firm* — Kilpatrick Townsend & Stockton LLP

(57) ABSTRACT

A wearable garment for recovery of a wearer after the wearer has undergone a surgical procedure, the wearable garment having an outer shell including at least a back panel and two front panels that, when the wearable garment is worn about a wearer, have outer edges that are adjacent to each other, a fastening system for securing the outer edges of the front panels together, thereby securing the wearable garment about the wearer, a compression region that provides a compressive force about the wearer; straps that hold the wearable garment about the wearer, and a tubing pocket attached to an inner surface of a respective one of the front panels for holding a drain tube in a coiled configuration against the wearer.

18 Claims, 10 Drawing Sheets

(56) References Cited

U.S. PATENT DOCUMENTS

| | | | |
|---|---|---|---|
| 2016/0066624 A1* | 3/2016 | Blackwell | A41C 3/02 |
| | | | 450/58 |
| 2017/0135847 A1* | 5/2017 | Leibowitz | A61F 5/4408 |
| 2018/0338551 A1* | 11/2018 | Stephens | A61F 5/03 |
| 2018/0360133 A1* | 12/2018 | Blackwell | A41C 3/0064 |
| 2020/0107588 A1* | 4/2020 | Smith | A41C 3/02 |
| 2022/0095703 A1* | 3/2022 | Razdan | A41C 3/0064 |

* cited by examiner

POST OPERATION MASTECTOMY BRA

CROSS-REFERENCE TO RELATED APPLICATION

This patent application claims priority to U.S. Provisional Patent Application Ser. No. 62/794,767, filed Jan. 21, 2019, and to International Patent Application No. PCT/US2020/014387, filed Jan. 21, 2021, the disclosures of which are incorporated herein by reference in their entirety.

FIELD OF INVENTION

The subject matter disclosed herein generally relates to post-operative garments useful in aiding in the recovery of patients after having undergone one or more surgical procedures. More particularly, the subject matter disclosed herein relates to a post-operative mastectomy bra that will aid in the recovery of patients after surgery of single or double mastectomies, breast reconstructions, breast augmentations, breast lifts, breast reductions, and the like.

BACKGROUND

One in eight women will be diagnosed with breast cancer over the course of her lifetime in the United States. As healthcare services will always be needed by patients for the diagnosis and treatment of breast cancer, new advancements are made continuously in the search for a cure for breast cancer. However, a lack of advancements in post operation medical support devices for patients having a mastectomy on one or both breasts has left a major gap in the reconstructive industry. Currently known mastectomy bras lack needed functionality that can reduce the risk of complications and provide a more comfortable recovery for patients during recovery from surgery. For example, many mastectomy bras have neither adjustable bands to provide variable compression to the patient and/or the ability to securely manage tubing that is secured within the chest cavity of a post-operative patient for fluid drainage. As such, a need currently exists to address these and other disadvantages prevalent in other currently known post-operative mastectomy bras.

SUMMARY

This specification discloses embodiments of wearable garments for recovery of a wearer after the wearer has undergone a surgical procedure, an example wearable garment can comprise: an outer shell comprising at least a back panel and two front panels that, when the wearable garment is worn about a wearer, have outer edges that are adjacent to each other; a fastening system for securing the outer edges of the front panels together, thereby securing the wearable garment about the wearer; a compression region configured to provide a compressive force about the wearer; straps that are configured to hold the wearable garment about the wearer; and a tubing pocket attached to an inner surface of a respective one of the front panels for holding a drain tube in a coiled configuration against the wearer.

In some embodiments of the wearable garment, the surgical procedure is a single mastectomy, a double mastectomy, a breast reconstruction, a breast augmentation, a breast lift, and/or a breast reduction.

In some embodiments, the wearable garment comprises a drain pocket configured to hold a drainage device connected to a first end of the drain tube, wherein the drainage device is configured to suction fluid from a surgical site of the wearer through the drain tube.

In some embodiments, the wearable garment comprises a slot formed through the respective one of the front panels, wherein the slot is configured such that the drain tube can pass through the slot, from an interior of the wearable garment to an exterior of the wearable garment, to allow fluid from the surgical site to be transported via the drain tube for storage in the drainage device in the drain pocket.

In some embodiments of the wearable garment, at least a front panel of the drain pocket comprises a mesh material or a transparent material configured such that an amount and/or color of the fluid within the drainage device can be monitored without removing the drainage from the drain pocket.

In some embodiments of the wearable garment, the drain pocket is removably attached to the garment at the compression region.

In some embodiments of the wearable garment, the straps have a length that is adjustable and can be detached from the outer shell at one of the front panels and/or the back panel.

In some embodiments of the wearable garment, the wearable garment is configured to be worn about the torso of the wearer and, when one of the straps is disconnected from the front panel, an upper edge of the front panel is foldable in a downward direction to allow for inspection of a surgical site adjacent a breast of the wearer without removing an entirety of the wearable garment from the torso of the wearer.

In some embodiments of the wearable garment, an amount of compression provided about the torso of the wearer by the straps is adjustable by adjusting the length of one or both straps.

In some embodiments of the wearable garment, the compression region comprises a compression band comprising an elastomeric material, the compression band being at a bottom edge of the outer shell.

In some embodiments, the wearable garment comprises an attachment surface attached on an external surface of the compression band and an attachment flap pivotably attached to the external surface of the compression band and spaced apart from the attachment surface along a circumference of the compression band, wherein the attachment flap is configured such that, when pulled towards the attachment surface, an effective length of the compression band is decreased, thereby increasing a magnitude of the compression force provided at the compression region.

In some embodiments of the wearable garment, the attachment flap is attached to the compression band vertically under the back panel of the outer shell and wherein the attachment surface is attached under one of the front panels of the outer shell.

In some embodiments of the wearable garment, the attachment surface and the attachment flap comprise respective hook-and-loop connection materials.

In some embodiments, the wearable garment comprises: a first attachment surface attached on an external surface of the compression band; a first attachment flap pivotably attached to the external surface of the compression band, wherein the first attachment flap is spaced apart from the attachment surface along a circumference of the compression band; a second attachment surface attached on the external surface of the compression band at a position different from the first attachment surface; and a second attachment flap pivotably attached to the external surface of the compression band, wherein the second attachment flap is spaced apart from the attachment surface in a direction along the circumference of the compression band different from that in which the first attachment flap is spaced apart from the first attachment surface; wherein the first and second attachment flaps are configured such that, when pulled towards the first and second attachment surfaces, respectively, an effective length of the compression band is decreased, thereby increasing a magnitude of the compression force provided at the compression region.

In some embodiments of the wearable garment, the first and second attachment flaps are attached to the compression band under at vertically under the back panel of the outer shell, wherein the first attachment surface is attached under one of the front panels of the outer shell, and wherein the second attachment surface is attached under another of the front panels of the outer shell.

In some embodiments of the wearable garment, the fastening system comprises, attached to the outer edge of a first of the front panels, a plurality of eyes that are vertically arranged in a first row and, attached to the outer edge of a second of the front panels, a plurality of hooks that are vertically arranged in a row, each hook being configured to engage with a vertically aligned one of the eyes to secure the garment about the wearer.

In some embodiments of the wearable garment, the plurality of eyes comprises at least a second row of vertically arranged eyes, a spacing between eyes of the second row being the same as eyes of the first row, wherein the hooks are configured such to engage with one of the vertically aligned eyes of the first or second row.

In some embodiments of the wearable garment, the fastening system comprises a zipper having a first zipper portion on the first of the front panels and a second zipper portion on the second of the front panels, the zipper being configured to prevent the hooks from being disengaged from the eyes while the first and second zipper portions are interlocked along a length thereof.

In another embodiment, a wearable garment for recovery of a wearer after the wearer has undergone a surgical procedure is disclosed, the wearable garment comprising: an outer shell comprising at least a back panel and two front panels that, when the wearable garment is worn about a wearer, have outer edges that are adjacent to each other; a fastening system for securing the outer edges of the front panels together, thereby securing the wearable garment about the wearer; a compression region configured to provide a compressive force about the wearer and comprising: a compression band made of an elastomeric material, the compression band being at a bottom edge of the outer shell; an attachment surface attached on an external surface of the compression band; and an attachment flap pivotably attached to the external surface of the compression band and spaced apart from the attachment surface along a circumference of the compression band, wherein the attachment flap is configured such that, when pulled towards the attachment surface, an effective length of the compression band is decreased, thereby increasing a magnitude of the compression force provided at the compression region; straps that are configured to hold the wearable garment onto the wearer; a tubing pocket attached to an inner surface of a respective one of the front panels for holding a drain tube in a coiled configuration against the wearer; a drain pocket configured to hold a drainage device connected to a first end of the drain tube, wherein the drainage device is configured to suction fluid from a surgical site of the wearer through the drain tube; and a slot formed through the respective one of the front panels, wherein the slot is configured such that the drain tube can pass through the slot, from an interior of the wearable garment to an exterior of the wearable garment, to allow fluid from the surgical site to be transported via the drain tube for storage in the drainage device in the drain pocket.

In some embodiments of the wearable garment, the slot is formed at the compression band so that none of the drain tube, other than a portion thereof having a length substantially a same as a distance between the slot and an upper edge of the attachment flap, is externally accessible when the garment is being worn by the wearer.

DETAILED DESCRIPTION

This specification discloses an example embodiment of a wearable post-operative garment in the form of a recovery garment, generally designated 100, which in the example embodiment shown is in the form of a mastectomy bra that is suitable for aiding in post-operative recovery of patients after surgical removal of one or both breasts, for example, to as a result of a diagnosis of breast cancer.

Figure 1:
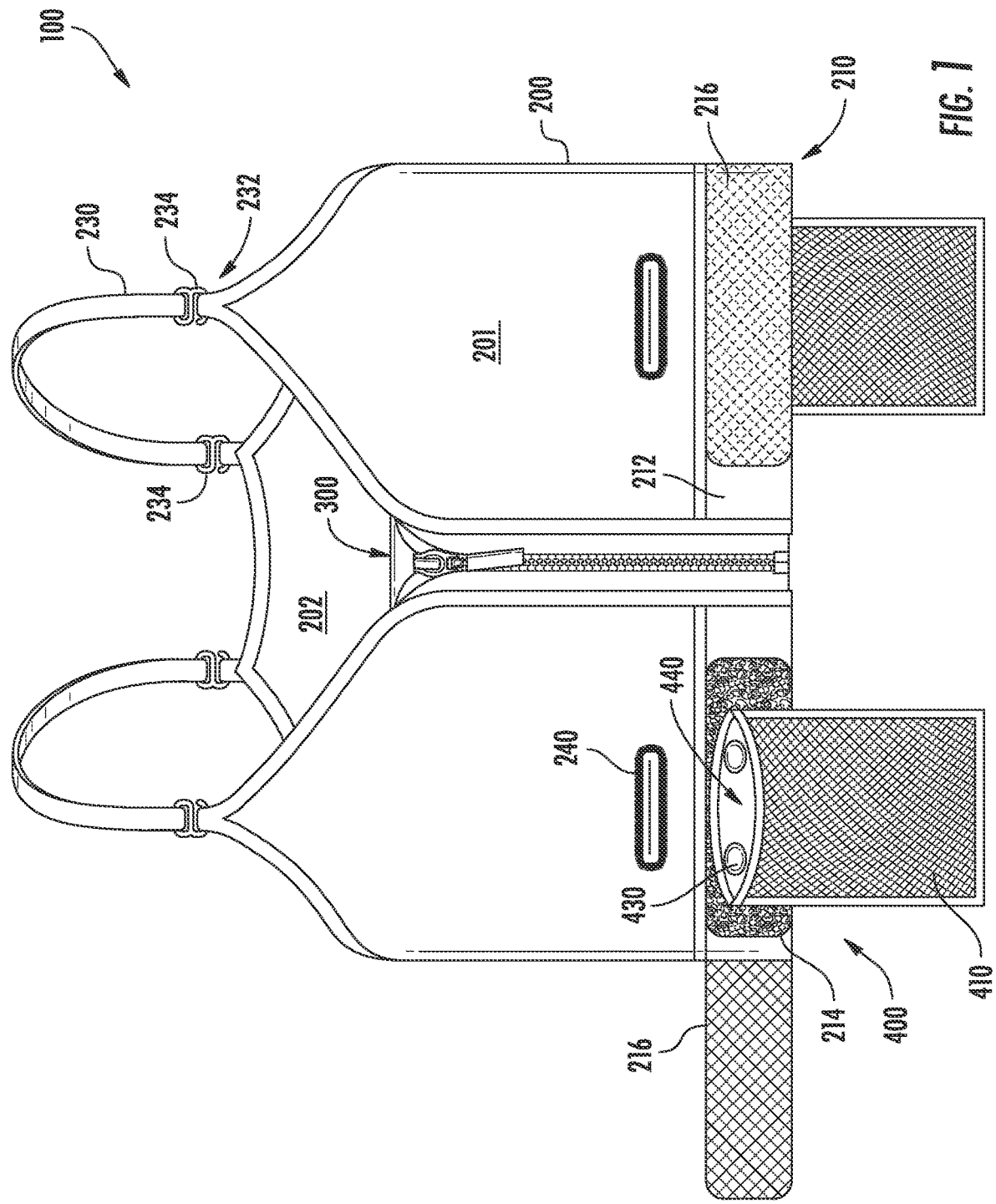
FIG. 1 is a front view of an example embodiment of a recovery garment (e.g., a bra) suitable for use, for example, in patients having undergone a mastectomy procedure.

FIG. 1 is a front view of the recovery garment 100, which has an outer shell 200 having two front panels 201 that are joined together at edges that are adjacent to each other, in the view shown in FIG. 1, by fastening system 300, and are joined together at the edges that are not adjacent to each other by a back panel 202. In some embodiments, the front panels 201 can be formed from separate pieces of fabric from the fabric used to form the back panel 202 and assembled together, e.g., by sewing the front panels 201 and the back panel 202 together at lateral edges of the back panel 202. The front panels 201 can be made from the same or a different fabric than the back panel 202. In some embodiments, the front panels 201 and the back panel 202 can be assembled together from a single piece of fabric, such that the resulting garment 100 will be devoid of any seams that may cause user discomfort when the garment 100 is worn for an extended period of time. Regardless of whether the same or different fabrics are used in forming the front panels 201 and the back panel 202 of the outer shell 200, it is advantageous for the fabric(s) used in their construction to be a suitable stretchy fabric, e.g., a fabric having some elastomeric fibers woven therein, that will cause a compressive force to be generated against the skin of the wearer to prevent unwanted shifting and fluid accumulation of the skin at locations where the surgery was performed, which can lead to post-operative pain and increased risk of infection.

The garment 100 comprises a compression region, generally designated 210, at a lower edge thereof. It should be noted that the outer shell 200 may extend beyond the compression region 210, as desired. At the compression region 210, the garment 200 has a compression band 212 that extends from one side of the fastening system 300 to the side of the fastening system 300, such that the compression band 212 extends entirely around the garment 200, including across the width of both front panels 201 and also across the back panel 202. In some embodiments, the compression band 212 is segmented, such that each front panel 201 and back panel 202 has a portion of the compression band 212 that, when the front and back panels 201, 202 are sewn together, the compression band 212 is also sewn together to substantially encircle the entirety of the torso of the wearer of the garment 100. It is advantageous for the compression band 212 to be made from a stretchable material, e.g., a material having an elastomeric fiber component woven therein. In some embodiments, the compression band 212 may be configured to be stretched by at least 25% of the unstretched length when worn by the wearer to generate a compressive force on the torso of the wearer.

In some embodiments, it is advantageous to provide for auxiliary compression to the torso of the wearer than can be generated by the compression band 212 alone. As such, in the embodiment shown, the compression band has an attachment surface 214, which can be made of "loop fabric" or "hook fabric" in the manner of hook-and-loop fabric (e.g., of the kind marketed under the trade name Velcro®), the attachment surface 214 being attached, e.g., sewn, onto an outer surface of the compression band 212 on both front panels 201. The compression band 212 also has a corresponding attachment flap 216, which can be made of whichever of the "loop fabric" or the "hook fabric" the attachment surface 214 is not made from, attached at a predetermined position on the compression band 212 of the back panel 202, such that a portion of the attachment flap 216 is secured to the compression band 212 and a majority of the attachment flap 216 can be moved independent of the compression band 212, such that this free portion of the attachment flap 216 can pivot about the secured portion of the attachment flap 216 in the manner of a hinge.

When the garment 100 is configured to be worn about the torso of a wearer, the wearer of the garment, or a person aiding the wearer of the garment 100, as the case may be, may grasp the free portion of the attachment flap 216 and pull the entire attachment flap 216 towards the attachment surface 214 so that at least a portion of the attachment flap 216 will can be secured to the attachment surface 214 where the attachment flap 216 overlaps the attachment surface. This pulling of the attachment flap 216 towards the attachment surface 214 pulls the portion of the compression band 212 wherein the attachment flap 216 is attached thereto, closer to the portion of the compression band 212 where the attachment surface 214 is attached, thereby effectively shortening the distance along the compression band 212 between the points where the attachment flap 216 and the attachment surface 214 are attached.

It is this effective shortening of the length of the compression band 212 that allows the garment 100 to be able to provide a variable amount of compression to the wearer at the compression band 212. As such, the amount of compression provided by the compression band 212 can be altered by changing the distance of the compression band 212 between where the attachment flap 216 and the attachment surface 214 are affixed thereto. This is advantageous because, during the post-operative healing process, as swelling decreases, the garment 100 can begin to fit more loosely than it should. As such, the degree by which the compression band 212 needs to be shortened in the days and weeks post-surgery can increase as the swelling at the surgical site abates. Additionally, while the garment 100 will need to be manufactured in different sizes to be fitted about the torsos of wearers having various sizes, the ability of the effective length of the compression band 212 to be shortened allows for the number of sizes in which the garment 100 must be manufactured to be minimized and/or reduced than if the compression band 212 did not have a variable effective length.

In some embodiments, the compression band 212 may have a plurality of panels of attachment flap 216 and attachment surface 214 affixed thereto. In the embodiment shown in FIGS. 1-3, there are two attachment flaps 216 and attachment surfaces 214 attached substantially symmetrically about the compression band 212, for example, relative to the spine of the wearer.

Figure 2:
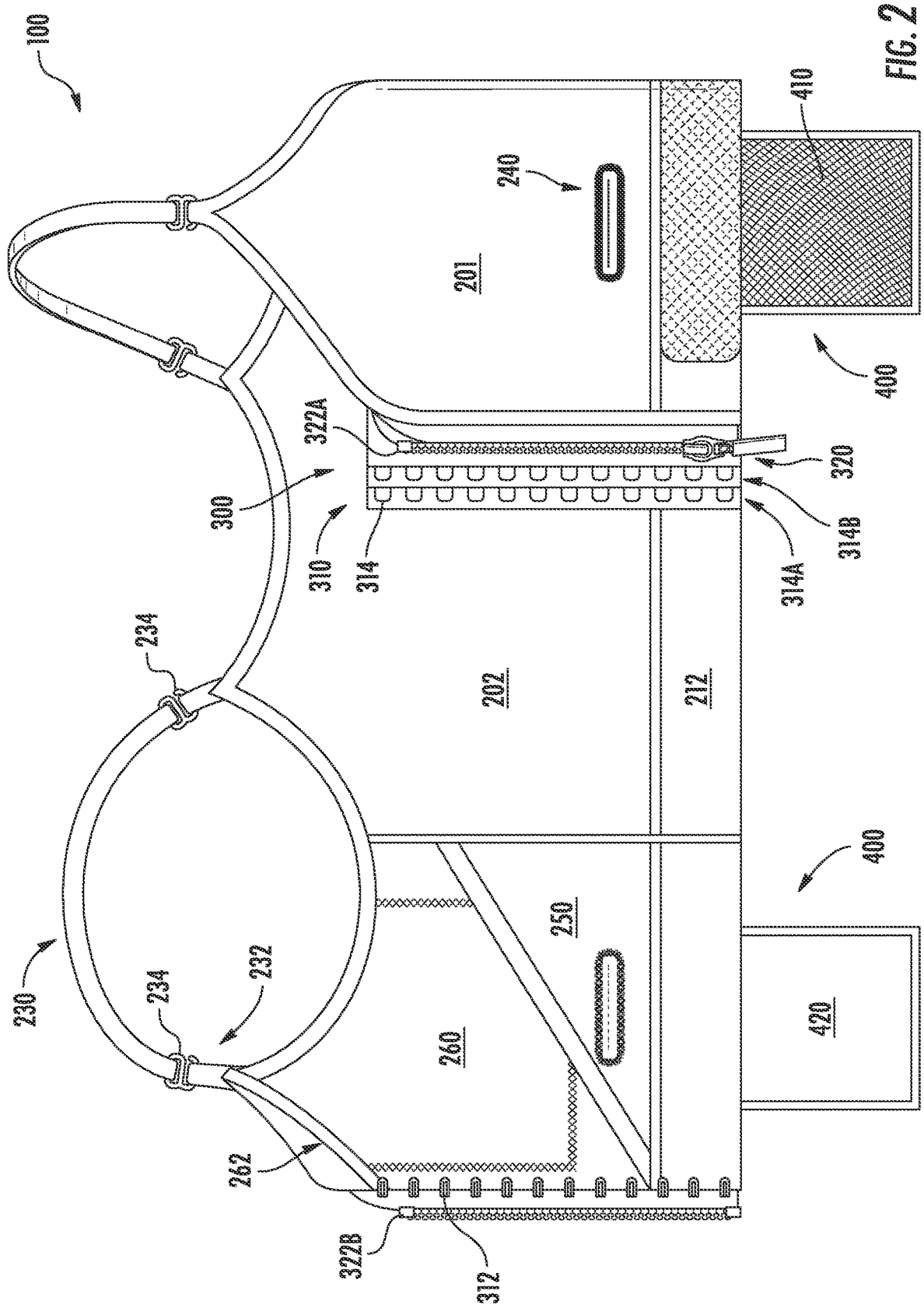
FIG. 2 is a partial internal view of the garment shown in FIG. 1, showing internal components associated therewith.
Figure 3:
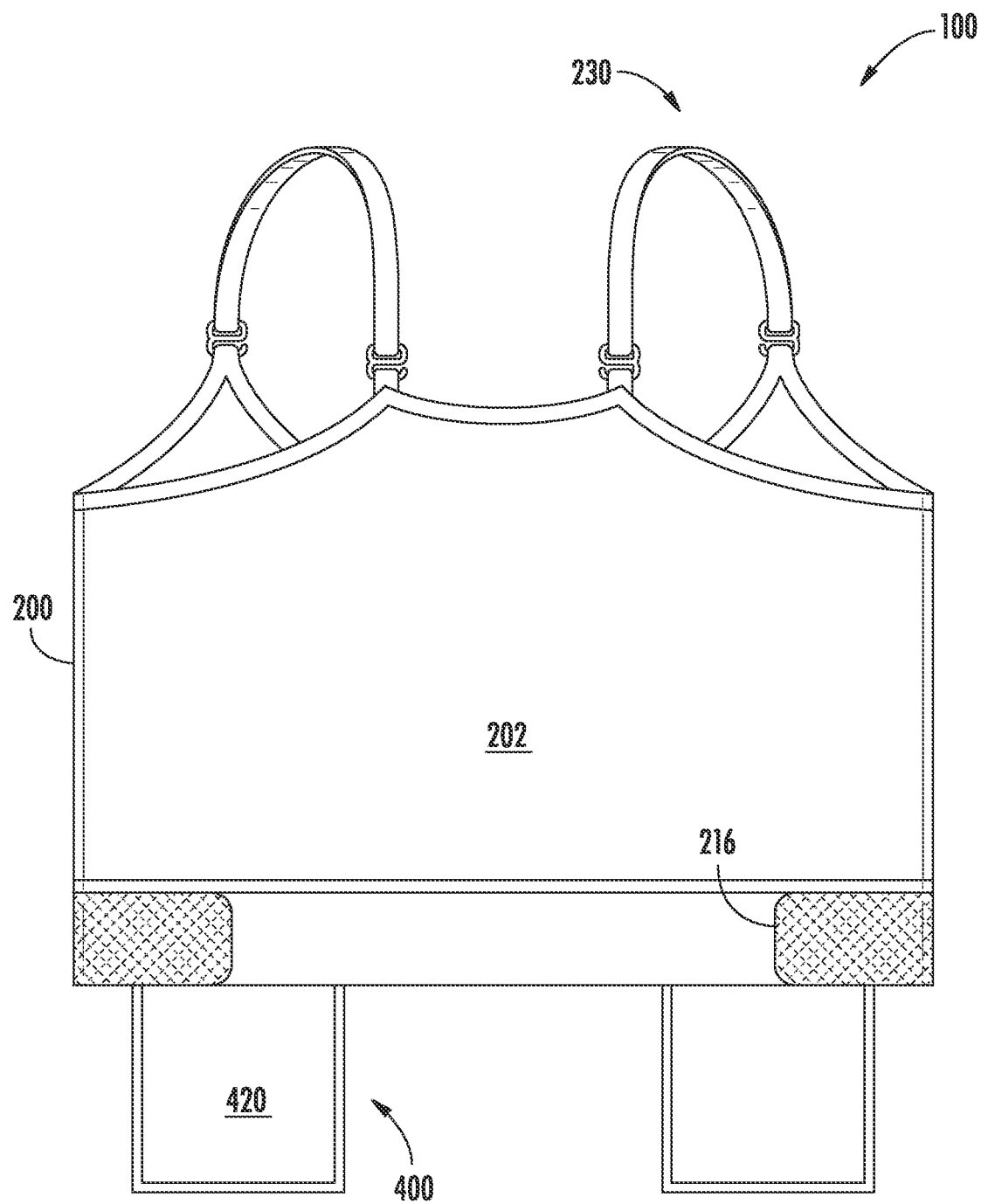
FIG. 3 is a rear view of the garment shown in FIG. 1.

The installation positions of the attachment flap 216 and the attachment surface 214 may be interchanged, such that the attachment flap 216 is rigidly connected along its length on a portion of the compression band 212 associated with one of the front panels 201 and only a portion of the attachment surface 214 is connected to a portion of the compression band 212 associated with the back panel 202 without deviating from the subject matter disclosed herein. While it is contemplated that the placements of the attachment flap 216 and the attachment surface 214 may be reversed, such that the attachment surface 214 were attached in the same manner as is shown in FIGS. 1-3 but on a portion of the compression band 212 associated with the back panel 202 and the attachment flap 216 may be attached in the same manner as is shown in FIGS. 1-3 but on a portion of the compression band 212 associated with one of the front panels 201, the illustrated configuration is advantageous because it allows for a wearer to more easily grasp the attachment flap 216 and adjust an amount of compression provided to the wearer by the garment 100 by changing the amount by which the attachment flap 216 overlaps the attachment surface 214. Additionally, the illustrated configuration allows for the garment 100 to be more readily fitted about the torso of the wearer immediately after the surgical procedure and before the wearer has been removed from the surgical environment due to the fact that the attachment flap 216 extends in the manner of flaps that would be readily accessible and extend outwardly from the torso of the wearer to allow for the effective length of the compression band 212 to be shortened to provide a desired amount of compression about the torso of the wearer. In some embodiments, the attachment flap 216 may be replaced with, for example, an elastic strap with hooks attached thereto and the attachment surface 214 may be replaced with, for example, sequential rows of eyes with which the hooks of the elastic strap may be engaged to effectively shorten the length of the compression band 212 and provide a desired amount of compression about the torso of the wearer. Other types of suitable mechanisms to shorten the effective length of the compression band 212 will be understood by those having ordinary skill in the art and do not deviate from the scope of the subject matter disclosed herein.

The garment 100 also has detachable straps, generally designated 230, which extend from an upper point on one of the front panels 201 to an upper point on the back panel 202, such that the straps 230 are able to pass over the shoulders of the wearer in the manner of shoulder straps. In the embodiment shown, the straps 230 do not cross each other and are attached to a same side of the back panel 202 as the front panel to which the strap 230 is attached. The straps 230 are removably attached to the front panel 201 and the back panel 202 at hooks 234 which removably attach the ends of the straps 230 to the garment 100 at attachment points 232, which can be in the form of loops fabric woven into the front and back panels 201, 202. The straps 230 may be made from an elastic material that can stretch and the length of the straps 230 can be adjusted.

In order to minimize the number of lengths of straps that must be provided, the straps can be attached to the garment in a configuration such that they cross each other across a back of the wearer. As such, a first strap 230 on the left side front panel 201 can be attached to either of the attachment points on the back panel 202, with a second strap 230 being attached to whichever attachment point on the back panel 202 to which the first strap is not attached. The length of the straps 230 is adjustable at one or both ends thereof. The straps 230 are fully detachable from the garment 100 to allow for the garment 100 to be fitted more easily to a wearer in a surgical environment, prior to the wearer regaining consciousness in recovery. For example, the straps 230 may be fitted over the shoulders of the wearer without requiring the arms of the wearer to be moved, thereby minimizing the movement of the wearer before the garment 100 is put on the wearer and reducing the incidence of complications within the first several (e.g., 2-5) days post-surgery.

The hooks 234 may be made from any suitable material, including, for example, plastic or metal. It is advantageous for the attachment point 232 on the front panel 201 where one end of the strap 230 is attached to be located near the collar bone, e.g., clavicle, of the patient when the garment 100 is being worn. This placement of the attachment point 232 near the collar bone allows for an easily accessible way of detaching the strap from the front panel 201 while the garment 100 is still being worn. As such, by detaching the strap 230 from one of the front panels 201, the upper part of that front panel 201 can be pulled down to allow for inspection of the surgical site, whether by the user or otherwise by a trained medical professional to ensure that proper healing is occurring without requiring removal of the garment 100, which can cause further trauma to the wearer at the surgical site during removal of the garment 100.

As noted herein, maintaining compression around the torso of the wearer at the surgical sites is important in reducing the risk of infection, for example, due to fluid accumulation post-surgery. Since the garment 100 can provide a variable amount of compression to the wearer at the surgical sites based on the stage of recovery at which the wearer is, the amount of fluid within the wearer at the surgical site(s) can be minimized, which thereby decreases the risk of infection. To ensure the garment 100 is installed to be sufficiently tight around the torso of the wearer, and also remains sufficiently tight to provide a therapeutically beneficial amount of compression at the surgical site(s), the garment 100 has a fastening system, generally designated 300, which has what is referred to herein as a double layer of compression where the garment 100 is secured about the torso of the patient.

The fastening system 300 includes hook-and-eye attachment, generally designated 310, and a zipper, generally designated 320. The hook-and-eye attachment 310 has a plurality of vertically arranged eyes 314 attached to one of the front panels 201 of the garment 100. A plurality of vertically arranged hooks 312 are attached to the other of the front panels 201. The vertical spacing and/or positioning of the hooks 312 is substantially the same as that of the eyes 314. As such, for each eye 314 in a row of eyes 314, there is a correspondingly positioned hook 312, such that there is one hook 312 for each eye 314 in a single row of eyes 314. In the example embodiment shown, there are two rows of hooks 314, with the amount of compression provided by the garment 201 being able to be varied based on which row of eyes 314 the hooks 312 are secured to. In some embodiments, more than two rows of eyes 314 may be provided. In some embodiments, a plurality of rows of hooks 312 can also be provided. The fastening system 300 also has a zipper 320, including a first zipper portion 322A which is attached substantially vertically along the same edge of the front panel 201 to which the rows of eyes 314 are attached, this being the substantially vertical edge of the front panel 201 by which the front panel 201 is not attached to the back panel 202. The zipper 320 also includes a second zipper portion 322B, which is attached substantially vertically along the same edge of the front panel to which the hooks 312 are attached, this being the substantially vertical edge of the front panel 201 by which the front panel 201 is not attached to the back panel 202. The hooks 312 and eyes 314 of the hook-and-eye attachment 310 are located behind the zipper 320 of the garment 320, such that substantially all, e.g., the majority, of the hook-and-eye attachment 310 cannot be seen when the first and second zipper portions 322A, 322B are interlocked to secure the garment 100 about the torso of the wearer. This arrangement of the hook-and-eye attachment 310 within the zipper 320 is advantageous, because it allows the garment 100 to be pulled tighter about the torso of the wearer, using the zipper 320, after the hooks 312 are engaged with one of the rows of the eyes 314 of the hook-and-eye attachment 310.

Within the interior of the outer shell 200 of the garment, and on an internal surface of one or both front panels 201, the garment 100 has internal pockets 260 defined therein. These internal pockets 260 are advantageously accessible by the wearer, due to the stretchy, e.g., elastic, nature of the front and/or rear panels 201, 202 of the outer shell, without having to remove the garment 100. As shown in FIG. 2, the respective inlet 262 by which each internal pocket 260 is able to be accessed is located adjacent an upper edge of the front panel, preferably between the attachment point 232 by which one strap 230 is attached to the front panel 201, and the fastening system 300, by which the front panels 201 are securely attached together. It is advantageous for the inlet 262 of the internal pocket 260 to be spaced apart from the uppermost edge of the front panel to hide the inlet 262 from view when the garment 100 is attached about the torso of the wearer. The internal pockets 260 are attached to the interior of the front panels 201 at a position to overlap the surgical site(s). The internal pockets 260 advantageously extend vertically down and laterally over to a position within the front panel 201 sufficient to ensure that the extent of the internal pocket 260 will be coincident with the surgical site(s) on the wearer. In some embodiments, the internal pocket 260 can extend as far down the front panel as to be coincident with the compression band 212 and as far laterally as where the front panel 201 transitions to the back panel 202, whether at a seam or not.

The internal pockets are configured to allow, for example, an ice pack 500 to be placed over the surgical site to reduce post-operative swelling and/or for a breast prosthesis to be installed over the surgical site once it is no longer therapeutically necessary to apply an ice pack 500 to the surgical site. As used herein, the term "ice pack" can be any therapeutic device which applies cold to, e.g., removes heat from, the surgical site. The ability to install a breast prosthesis within the internal pocket 260 after the application of an ice pack 500 is no longer therapeutically necessary is advantageous because the use of such prostheses can complement the wearer's post-surgical physical appearance and allow the wearer to begin to return to a sense of normalcy by more closely resembling the pre-surgery appearance of the wearer before the wearer undergoes reconstructive surgery and allows for further healing to take place without the wearer feeling the need to rush into such reconstructive surgery, which can lead to increased risks of post-operative complications when reconstructive surgery is attempted close in time to, or simultaneous with, the mastectomy surgery.

Figure 4:
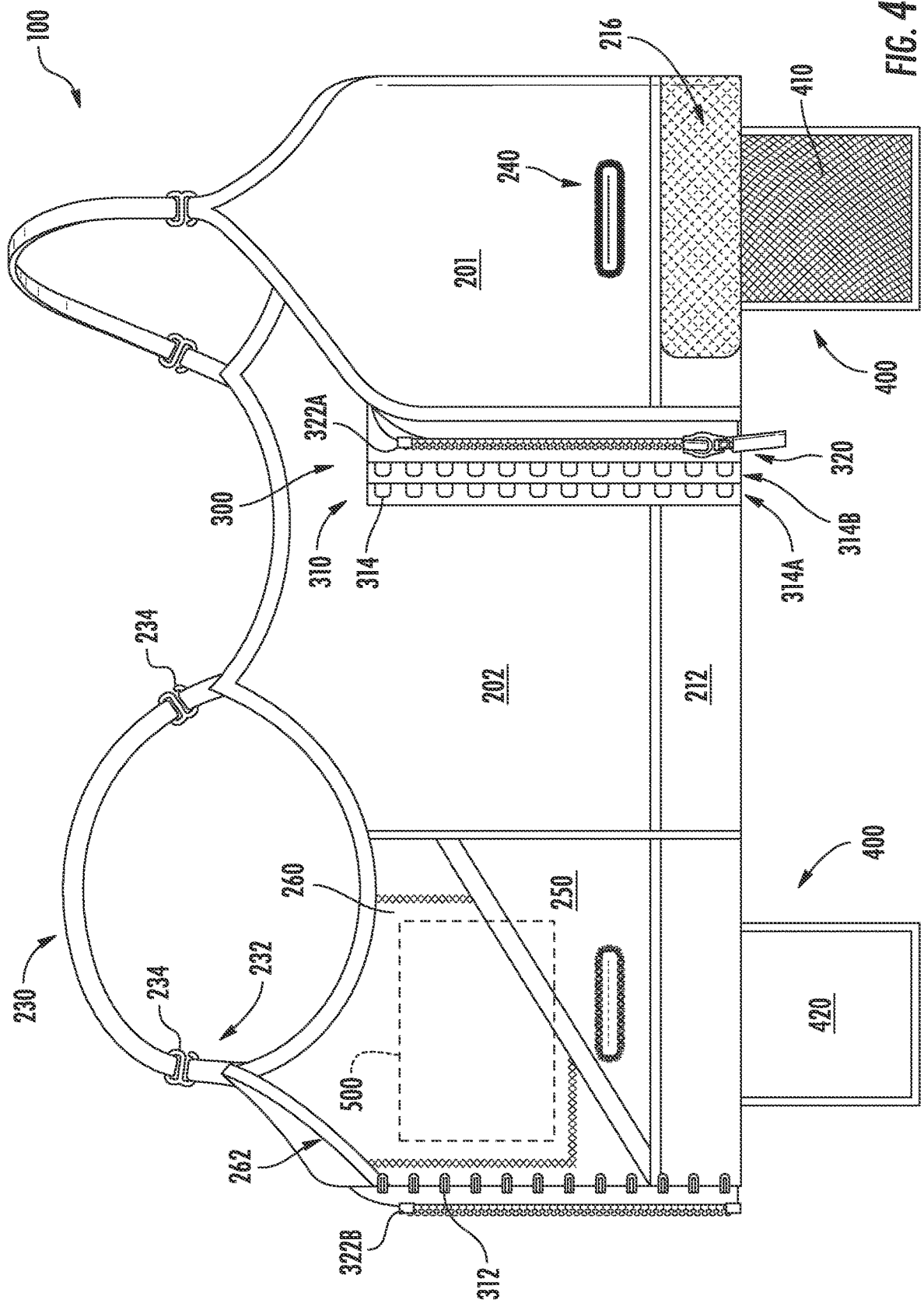
FIG. 4 is a partial internal view of the garment shown in FIG. 1, showing further aspects of the garment.
Figure 5:
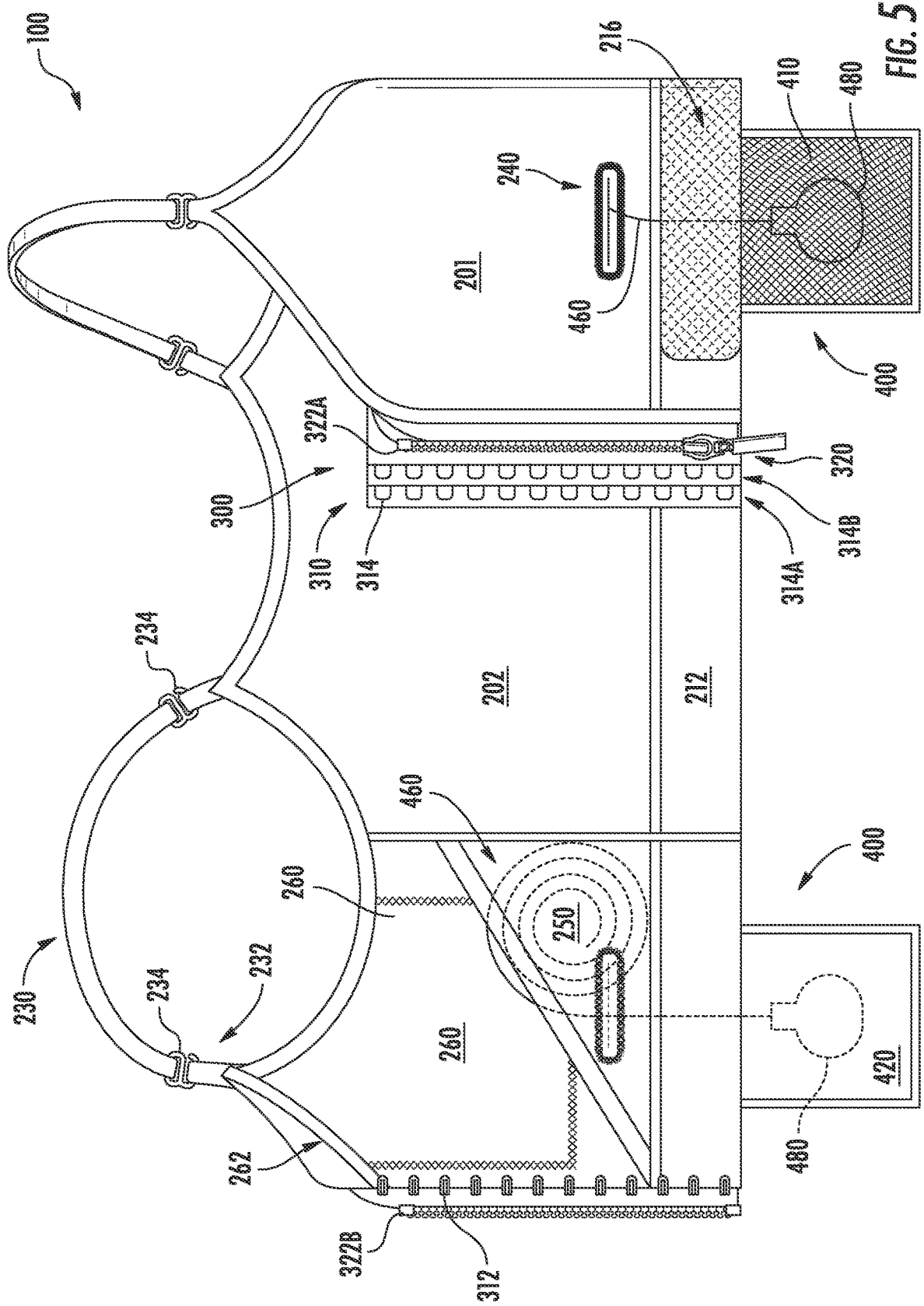
FIG. 5 is a partial internal view of the garment shown in FIG. 1, showing still further aspects of the garment.

As shown in FIGS. 2, 4, and 5, the outer shell 200 has, on an internal surface of one or both front panels 201, a tubing pocket 250, which is configured to hold a coiled drain tube, generally designated 460, therein to prevent the tubing from becoming entangled with anything else. The drain tube 460 is inserted at a first end thereof within the torso (e.g., under the armpit) of the wearer of the garment 100 to allow for fluid to drain from the surgical site rather than accumulating within the torso of the patient during the healing process, thereby reducing post-operative complications due to, for example, infection. It is advantageous to have the drain tube 460 contained securely within the pocket 250 of the garment so that the drain tube 460 will not become entangled with other objects in the surroundings of the wearer, or otherwise be exposed so as to be inadvertently pulled out from the surgical site, a very painful occurrence that requires the wearer to undergo further medical procedures to reinsert the drain tube 460 in the surgical site and which can also lead to increased incidents of complications for the wearer.

The drain tube 460 can be any type of tubing. In one or both of the front panels 201, a slot, generally designated 240, is formed to allow for passage of objects, including the tubing, between the interior and the exterior of the garment 100 through the front panel 201 in which the slot 240 is formed. As shown in FIG. 5, the drain tube 460 is connected at a second end to a drainage device 480, which can be a suction bulb that can be squeezed to create a vacuum to promote fluid removal from the surgical site, and/or can be any other suitable device for promoting fluid removal from the surgical site within the torso of the wearer. Once connected to the drainage device 480, any excess drain tube 460 can be coiled up rather than being allowed to dangle between the point at which the first end of the drain tube 460 is attached to the torso of the wearer and the drainage device 480, this coiled up portion of drain tube 460 is placed within the tubing pocket 250 and only the portion of the drain tube 460 between the slot 240 and the hook fabric 216 is accessible from the exterior of the garment 100.

Since the tubing pocket 250 is located in the interior of the front panel 201 of the garment 100, it is advantageous in some embodiments for the slot 240 to be of a size that allows for the drainage device to be pushed through the slot 240, for example, without detaching the drainage device 480 from the drain tube 460. It is further advantageous for the slot 240 to be located within, or at least adjacent to, the tubing pocket 250. As used herein, the term "adjacent to" can be defined as being formed in the front panel 201 to which the tubing pocket 250 is attached on an interior surface thereof, but outside of an outer periphery of the internal pocket 260 of the same front panel 201. To minimize the length of exposed drain tube 460, it is advantageous for the slot to be formed as close to the compression band 212 as possible. In some embodiments, the tubing pocket 250 is made at least partially from a stretchable material (e.g., a material having a spandex, or elastomeric thread component) that will allow for easy insertion and removal of the coiled drain tube 460 by the wearer of the garment 100, while also providing a comfortable contact surface against the skin of the wearer. The tubing pockets 250 are secured to the interior of the front panel 201, for example, by stitching and/or sewing, to ensure that the drain tube 460 is held securely against the torso of the wearer of the garment 100. As noted elsewhere herein, the tubing pockets 250 are particularly advantageous in limiting the exposure of the drain tube 460 to the outside environment, thereby preventing the drain tube 460 from becoming entangled with any objects in the immediate vicinity of the wearer of the garment 100, thereby advantageously reducing the risk that the drain tube 460 will be caught, pulled, or torn away from the location where the drain tube 460 is fixedly attached (e.g., by surgical sutures) to the torso of the wearer of the garment 100.

Drain pockets, generally designated 400, are removably attached to the garment 100 in a position where the drainage device 480 can be held in place while remaining securely attached to the end of the drain tube 460 that passes through the slot and is located external to the garment 100. In the example embodiment shown, the drain pockets 400 are attached vertically beneath the slot 240 from which the drain tube 460 to which the drainage device 480 is connected. The drain pockets 400 have a drain pocket front panel 410 and a drain pocket back panel 420, which can be made of the same or different fabrics. In the example embodiment shown, the drain pocket front panel 410 is made of a mesh material, so that the amount and/or color of the fluid within the drainage device 480 can be visually determined without the drainage device 480 having to be removed from the drain pocket 400. In the example embodiment shown, the drain pocket back panel 420 is made of a substantially solid material, which can be a stretchy and/or elastomeric material, which is contemplated as being more rugged than the mesh material of the drain pocket front panel 410. In some embodiments, the drain pocket front and/or back panels 410, 420 may be made from a transparent or translucent plastic sheet. The drain pockets 400 have an opening, generally designated 440, at the top when the drain pocket 400 is attached to the garment 100, the opening 440 allowing for insertion and removal of the drainage device 480 from the drain pocket 400. In some embodiments, the opening 440 is open. In another embodiment, the opening 440 is configured to be closed, at least partially, for example using an elastic band contained and/or sewn within the portion of the fabric of the drain pocket 400 that defines the opening 400, such a constricted opening 440 being advantageous in that it resists removal of the drainage device 480 from the pocket unless removed by the wearer and/or a medical professional providing post-operative care to the wearer. In some embodiments, the drain pocket back panel 420 has a portion of an internal and/or external surface thereof that is made of hook fabric or loop fabric, so that the drain pocket 250 can be secured directly between the attachment flap 216 and the attachment surface 214 on the compression band 212. In some embodiments, an elastic band may be provided about the circumference of the opening 440 of the drain pockets 400 that can be deformed (e.g., expanded) to allow for removal or insertion of a drainage device 480 from or in the drain pocket 400, but which has a non-deformed size that is smaller than the drainage device 480 to more securely hold the drainage device within the drain pocket 250.

The drain pockets 400 are, in the embodiment shown, attached to be accessible on the front of the garment 100, but may be attached to the garment 100 in any suitable position. The drainage pockets 400 are advantageously removably attachable to the garment 100, for example, at the compression band 212 in the embodiment shown. In the example embodiment shown, the drain pockets are attachable at the compression band 212 by snaps 430, which can also be in the form of buttons or any other suitable type of attachment, thereby allowing the drain pockets 250 to be removed from the garment 100 and the garment 100 to be worn without the drain pockets 250 after the drain tube 460 is removed from the surgical site, which will typically occur approximately 2 weeks after surgery in the case of a mastectomy. In the example embodiment shown, the drain pockets 400 are located on the front portion of the compression band 212 and extend beyond the compression band. Depending on the type of drainage device 480 needed during post-operative care, the drain pockets 400 can be of any suitable size and are interchangeable with drain pockets 400 of any other size. In some embodiments, the garment 100 can have two differently sized drain pockets 400 attached thereto about 5 inches from the bottom of the bra.

Various features of a second alternative embodiment of a recovery garment, generally designated 101, are shown in FIGS. 6-10. Structures and/or features that are designated with the same reference number in FIGS. 6-10 as was used in the description of any of FIGS. 1-5 are to be regarded as being substantially similar, or identical, to such structures and/or features of FIGS. 1-5, except to the extent that such structures and/or features may be described differently with respect to FIGS. 6-10. Furthermore, even if structures and/or features of the garment 101 of FIGS. 6-10 are described differently from the descriptions thereof in FIGS. 1-5, the structures and/or features of the garments 100, 101 may be interchanged readily to provide different combinations and further example embodiments of such a recovery garment and are not outside the scope of the subject matter disclosed and described herein.

Figure 6:
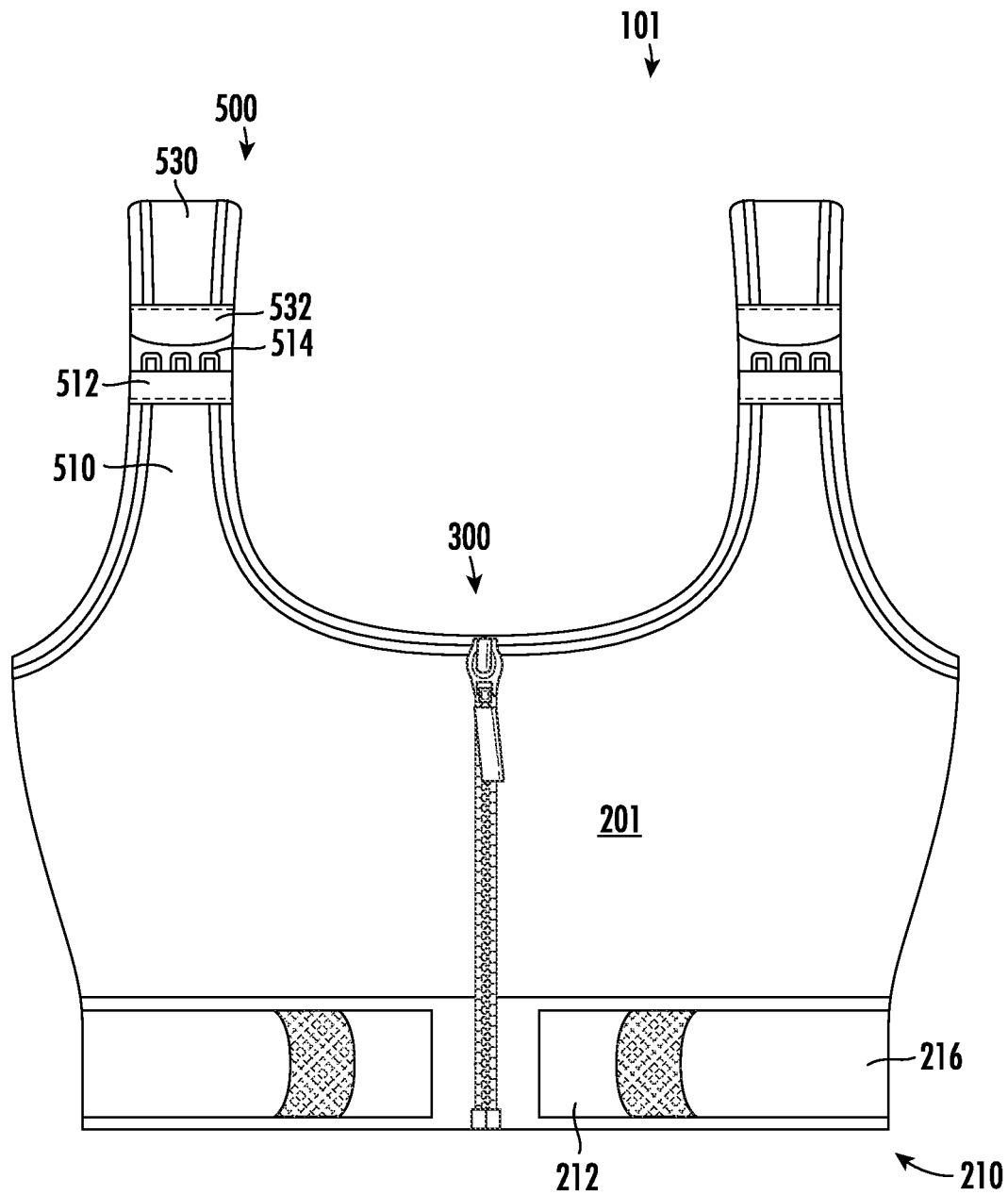
FIG. 6 is a front view of another example embodiment of a recovery garment (e.g., a bra) suitable for use, for example, in patients having undergone a mastectomy procedure.
Figure 7:
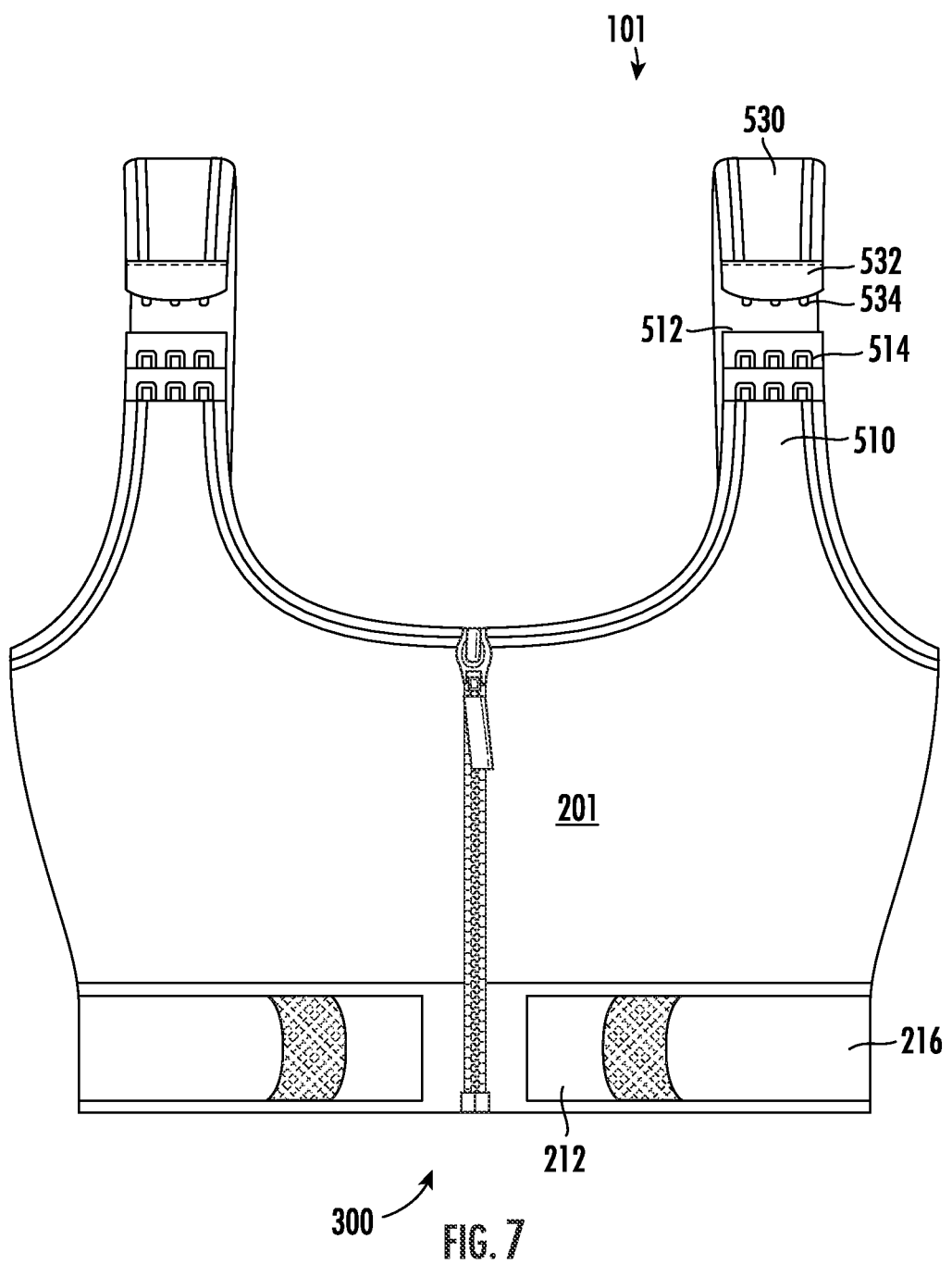
FIG. 7 is a front view of the garment of FIG. 6, with the straps disconnected to illustrate features of the attachment thereof.

Referring to FIGS. 6 and 7, a front view of a second example embodiment for a recovery garment, generally designated 101, is shown therein. Unlike the straps for the garment 100, the garment 101 has straps, generally designated 500, that provide an attachment between the front panel(s) 201 and the rear panel 202 (see, e.g., FIGS. 8 and 9) and are each configured to pass over one of the shoulders of the person wearing the garment 101 to secure the garment 101 over and about the upper torso of the wearer. Each strap 500 comprises a first strap portion 510, which is integrally formed with (e.g., in a monolithic, uninterrupted, and/or unitary manner) one of the front panels 201, and a second strap portion 530, which is integrally formed with (e.g., in a monolithic, uninterrupted, and/or unitary manner) the back panel 202. The first strap portion 510 comprises a first connector 512, which comprises a plurality of rings, or eyelets 514. The second strap portion 530 comprises a second connector 532, which comprises a plurality of hooks 534, each of which is positioned and configured to engage with one of the eyelets 514. In some embodiments, the positioning of the eyelets 514 and the hooks 534 on the respective first and second connectors 512, 532 can be reversed from the positions shown, such that the hooks 534 can be provided on the first connector 512 and the eyelets 514 the hooks 534 can be provided on the second connector 532.

As shown in at least FIG. 7, the eyelets 514 are generally rectangular in shape and are arranged in the form of a matrix, in which there are provided two (2) rows of eyelets 514, each row being spaced apart from adjacent rows of eyelets 514 (e.g., in the direction of extension of the strap 500) and comprising three (3) eyelets 514. That spacing apart of the rows of eyelets 514 is advantageous because it allows the first and second strap portions 510, 530 to be fastened together to provide different effective lengths of the strap, thereby allowing a single garment 101 to accommodate any of a plurality of different anatomy shapes and sizes. The number of eyelets 514 in each row can be any desired quantity and it is generally advantageous for the number of eyelets 514 in each row to correspond to (e.g., be the same as) the number of hooks 534 in the row of the second connector 532. In some embodiments, the hooks 534 may be provided in a plurality of rows of hooks 534 on the second connector, much the same as is described herein with respect to the rows of eyelets 514 of the first connector 512, such that rows of hooks 534 would be spaced apart from adjacent rows of hooks 534 (e.g., in the direction of extension of the strap 500). Thus, each strap 500 can have any suitable number of rows of hooks 534 and eyelets 514. In some embodiments, the first and second connectors 512, 532 comprise a fabric in the manner of hook-and-loop fabric, with the first connector 512 comprising the hook fabric and the second connector 532 comprising the loop fabric, or vice versa.

Figure 8:
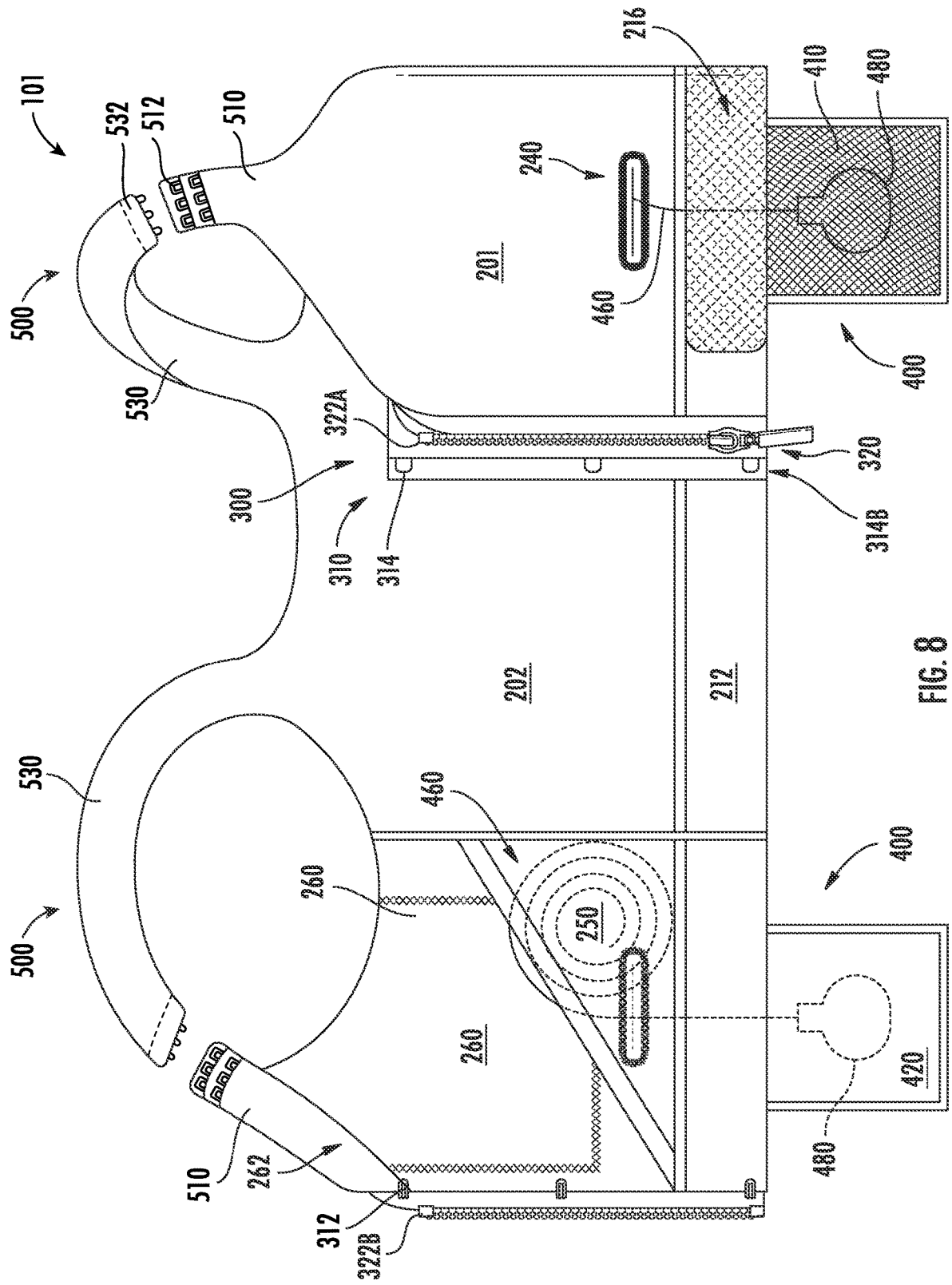
FIG. 8 is a partial internal view of the garment shown in FIG. 6, showing further aspects of the garment.

FIG. 8 shows not only the configuration of the straps 500, but also how the front panels 201 are attached together to secure the garment 101 on and about the upper torso of the wearer. The fastening system 300 is generally similar to that which is shown and described in garment 100, having a hook-and-eye attachment, generally designated 310, and a zipper, generally designated 320. The hook-and-eye attachment 310 has a plurality of vertically arranged eyes 314 attached to one of the front panels 201 (e.g., at a substantially vertical edge thereof, where the front panels 201 are joined together when the garment 101 is worn about the upper torso of the wearer, and by which the front panel 201 is not attached to the back panel 202) of the garment 101. A plurality of vertically arranged hooks 312 are attached to the other of the front panels 201. The vertical spacing and/or positioning of the hooks 312 is substantially the same as that of the eyes 314. As such, for each eye 314 in a row of eyes 314, there is a correspondingly positioned hook 312, such that there is one hook 312 for each eye 314 in a single row of eyes 314. In the example embodiment shown, there are only three (3) hooks 312 and only three (3) eyes 314 for each garment 101. In the example embodiment shown, the garment 101 to has a first hook 312 and a first eye 314 attached at a top edge (e.g., spaced apart therefrom by about 0.5 inches or less) of the respective front panel 201; a second hook 312 and a second eye 314 attached at a bottom edge (e.g., spaced apart therefrom by about 0.5 inches or less) of the respective front panel 201; and a third hook 312 and a third eye 314 attached to the respective front panel 201 at a position between the first and second hooks 312 and eyes 314, and preferably at or about a midpoint between the first and second hooks 312 and eyes 314. While the eyes 314 are shown attached to the front panel 201 in a position such that the eyes 314 extend beyond (e.g., are visible in the position shown in FIG. 8) the first zipper portion 322A, in some embodiments, the row of eyes 314 are attached in a position that in underneath (e.g., does not extend beyond, or has only a portion thereof that extends beyond) the first zipper portion 322A.

The fastening system 300 also has a zipper 320, including a first zipper portion 322A which is attached substantially vertically along the same edge of the front panel 201 to which the rows of eyes 314 are attached, this being the substantially vertical edge of the front panel 201 by which the front panel 201 is not attached to the back panel 202. The zipper 320 also includes a second zipper portion 322B, which is attached substantially vertically along the same edge of the front panel to which the hooks 312 are attached, this being the substantially vertical edge of the front panel 201 by which the front panel 201 is not attached to the back panel 202. The hooks 312 and eyes 314 of the hook-and-eye attachment 310 are located behind the zipper 320 of the garment 320, such that substantially all (e.g., the majority) of the hook-and-eye attachment 310 cannot be seen when the first and second zipper portions 322A, 322B are interlocked to secure the garment 100 about the torso of the wearer. This arrangement of the hook-and-eye attachment 310 within the zipper 320 is advantageous, because it allows the garment 100 to be pulled tighter about the torso of the wearer, using the zipper 320, after the hooks 312 are engaged with one of the rows of the eyes 314 of the hook-and-eye attachment 310.

Figure 9:
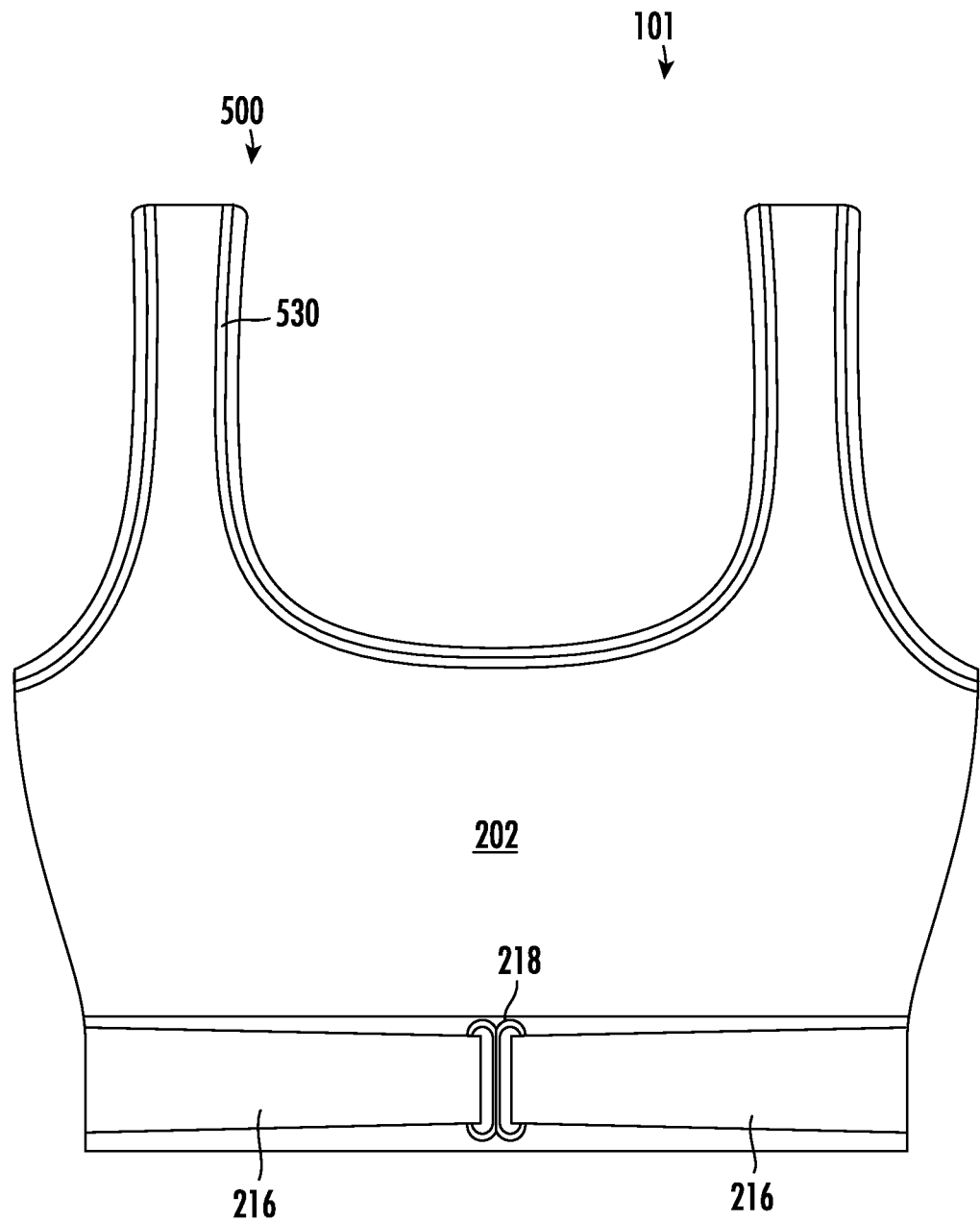
FIG. 9 is a rear view of the garment shown in FIG. 6.
Figure 10:
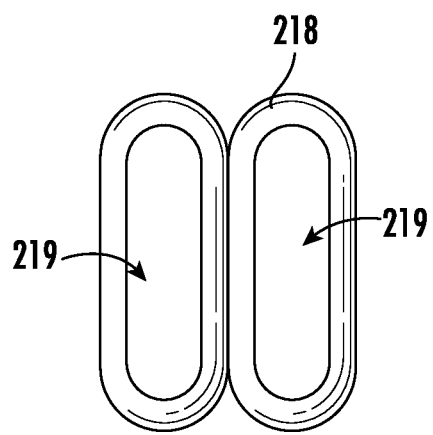
FIG. 10 is an isolated view of an element of the garment shown in FIG. 9, to provide further detail as to the structure thereof.

FIGS. 9 and 10 show aspects of how an attachment flap 216 can be provided in the manner of one or more straps that are attached to the garment 101 at the bottom edge thereof and are configured to act either in conjunction with the compression band 212 of the garment 100, or as a replacement for the compression band. The attachment flaps 216 are attached at the bottom edge of the back panel 202 (e.g., on the same side thereof as the front panel to which the attachment flap will be secured) and pass through the loop 218, which comprises two passages 219 therethrough and is shaped generally as a figure-eight. The attachment flaps 216 are advantageously made, at least partially, of an elastic material, such that the compression force provided by the attachment flap 216 increases as it elongates. Thus, the tension provided by each attachment flap 216 can be changed by stretching the attachment flap 216 and securing it at a further circumferential point on the attachment surface 214.

Other embodiments of the current invention will be apparent to those skilled in the art from a consideration of this specification or practice of the invention disclosed herein. Thus, the foregoing specification is considered merely exemplary of the current invention with the true scope thereof being defined by the following claims.

What is claimed is:

1. A wearable garment for recovery of a wearer after the wearer has undergone a surgical procedure, the wearable garment comprising:
    an outer shell comprising at least a back panel and two front panels that, when the wearable garment is worn about the wearer, have outer edges at each of the two front panels that are adjacent to each other;
    a fastening system configured to secure the outer edges of the front panels together, thereby securing the wearable garment about the wearer;
    a compression region configured to provide a compressive force about the wearer wherein the compression region comprises a compression band comprising an elastomeric material, the compression band being at a bottom edge of the outer shell and wherein the compression band further comprises an attachment surface attached on an external surface of the compression band and an attachment flap pivotably attached to the external surface of the compression band on the back panel portion of the compression band and spaced apart from the attachment surface along a circumference of the compression band;
    straps that are configured to hold the wearable garment about the wearer; and
    a tubing pocket attached to an inner surface of a respective one of the front panels configured to hold a drain tube in a coiled configuration against the wearer.

2. The wearable garment of claim 1, wherein the surgical procedure is a single mastectomy, a double mastectomy, a breast reconstruction, a breast augmentation, a breast lift, and/or a breast reduction.

3. The wearable garment of claim 1, comprising a drain pocket configured to hold a drainage device connected to a first end of the drain tube, wherein the drainage device is configured to suction fluid from a surgical site of the wearer through the drain tube.

4. The wearable garment of claim 3, comprising a slot formed through the respective one of the front panels, wherein the slot is configured such that the drain tube can pass through the slot, from an interior of the wearable garment to an exterior of the wearable garment, to allow fluid from the surgical site to be transported via the drain tube for storage in the drainage device in the drain pocket.

5. The wearable garment of claim 3, wherein at least a front panel of the drain pocket comprises a mesh material or a transparent material configured such that an amount and/or color of the fluid within the drainage device can be monitored without removing the drainage from the drain pocket.

6. The wearable garment of claim 3, wherein the drain pocket is removably attached to the garment at the compression region.

7. The wearable garment of claim 1, wherein the straps have a length that is adjustable and/or can be detached from the outer shell at one of the front panels and/or the back panel.

8. The wearable garment of claim 7, wherein the wearable garment is configured to be worn about the torso of the wearer and, when one of the straps is disconnected, an upper edge of the front panel is foldable in a downward direction to allow for inspection of a surgical site adjacent a breast of the wearer without removing an entirety of the wearable garment from the torso of the wearer.

9. The wearable garment of claim 8, wherein an amount of compression provided about the torso of the wearer by the straps is adjustable by adjusting the length of one or both straps.

10. The wearable garment of claim 1, wherein the attachment flap is configured such that, when pulled towards the attachment surface, an effective length of the compression band is decreased, thereby increasing a magnitude of the compression force provided at the compression region.

11. The wearable garment of claim 10, wherein the attachment flap is attached to the compression band along the width of the compression band on the back panel portion of the compression band and wherein the attachment surface is attached on the front panel portion of the compression band.

12. The wearable garment of claim 10, wherein the attachment surface and the attachment flap comprise respective hook-and-loop connection materials.

13. The wearable garment of claim 1, comprising:
    a first attachment surface attached on an external surface of the compression band;
    a first attachment flap pivotably attached to the external surface of the compression band on the back panel portion of the compression band, wherein the first attachment flap is spaced apart from the attachment surface along a circumference of the compression band;

a second attachment surface attached on the external surface of the compression band at a position different from the first attachment surface; and a second attachment flap pivotably attached to the external surface of the compression band on the back panel portion of the compression band, wherein the second attachment flap is spaced apart from the attachment surface in a direction along the circumference of the compression band different from that in which the first attachment flap is spaced apart from the first attachment surface;

wherein the first and second attachment flaps are configured such that, when pulled towards the first and second attachment surfaces, respectively, an effective length of the compression band is decreased, thereby increasing a magnitude of the compression force provided at the compression region.

14. The wearable garment of claim 13, wherein the first and second attachment flaps are attached along the width of the compression band on the back panel portion of the compression band, wherein the first and second attachment surfaces are attached on the front panel portion of the compression band.

15. The wearable garment of claim 1, wherein the fastening system comprises, attached to the outer edge of a first of the front panels, a plurality of eyes that are vertically arranged in a first row and, attached to the outer edge of a second of the front panels, a plurality of hooks that are vertically arranged in a row, each hook being configured to engage with a vertically aligned one of the eyes to secure the garment about the wearer.

16. The wearable garment of claim 15, wherein the plurality of eyes comprises at least a second row of vertically arranged eyes, a spacing between eyes of the second row being the same as eyes of the first row, wherein the hooks are configured such to engage with one of the vertically aligned eyes of the first or second row.

17. The wearable garment of claim 15, wherein the fastening system comprises a zipper having a first zipper portion on the first of the front panels and a second zipper portion on the second of the front panels, the zipper being configured to prevent the hooks from being disengaged from the eyes while the first and second zipper portions are interlocked along a length of the fastening system.

18. A wearable garment for recovery of a wearer after the wearer has undergone a surgical procedure, the wearable garment comprising:

an outer shell comprising at least a back panel and two front panels that, when the wearable garment is worn about the wearer, have outer edges at each of the two front panels that are adjacent to each other;

a fastening system configured to secure the outer edges of the front panels together, thereby securing the wearable garment about the wearer;

a compression region configured to provide a compressive force about the wearer and comprising:
  a compression band made of an elastomeric material, the compression band being at a bottom edge of the outer shell;
  an attachment surface attached on an external surface of the compression band; and
  an attachment flap pivotably attached to the external surface of the compression band on the back panel portion of the compression band and spaced apart from the attachment surface along a circumference of the compression band,
  wherein the attachment flap is configured such that, when pulled towards the attachment surface, an effective length of the compression band is decreased, thereby increasing a magnitude of the compression force provided at the compression region;

straps that are configured to hold the wearable garment onto the wearer;

a tubing pocket attached to an inner surface of a respective one of the front panels configured to hold a drain tube in a coiled configuration against the wearer;

a drain pocket removably attached to the outer shell at the compression band under each of the two front panels configured to hold a drainage device connected to a first end of the drain tube, wherein the drainage device is configured to suction fluid from a surgical site of the wearer through the drain tube; and a slot formed through the respective one of the front panels, wherein the slot is configured such that the drain tube can pass through the slot, from an interior of the wearable garment to an exterior of the wearable garment, to allow fluid from the surgical site to be transported via the drain tube to the drainage device configured to store fluid from the surgical site in the drain pocket.

* * * * *

UNITED STATES PATENT AND TRADEMARK OFFICE
CERTIFICATE OF CORRECTION

| | | |
|---|---|---|
| PATENT NO. | : 12,097,318 B2 | Page 1 of 1 |
| APPLICATION NO. | : 17/381878 | |
| DATED | : September 24, 2024 | |
| INVENTOR(S) | : Leah Brooke Wyrick | |

It is certified that error appears in the above-identified patent and that said Letters Patent is hereby corrected as shown below:

In the Specification

Under CROSS-REFERENCE TO RELATED APPLICATION – Column 1, Line 4, "filed Jan. 21, 2021" should read --filed Jan. 21, 2020--

Signed and Sealed this
Fourth Day of February, 2025

Coke Morgan Stewart
*Acting Director of the United States Patent and Trademark Office*